United States Patent [19]

Ward et al.

[11] Patent Number: 4,983,600

[45] Date of Patent: Jan. 8, 1991

[54] HETEROCYCLIC COMPOUNDS USEFUL AS 5-HT₃ ANTAGONISTS

[75] Inventors: Terence J. Ward, Maidenhead; Janet C. White, Wokingham; Gerald Bradley, Weybridge, all of England

[73] Assignee: John Wyeth & Brother Limited, Maidenhead, England

[21] Appl. No.: 421,920

[22] Filed: Oct. 16, 1989

Related U.S. Application Data

[63] Continuation-in-part of Ser. No. 288,732, Dec. 22, 1988, abandoned.

[30] Foreign Application Priority Data

Dec. 24, 1987 [GB] United Kingdom ............... 8730193
Aug. 19, 1988 [GB] United Kingdom ............... 8819728

[51] Int. Cl.$^5$ ............... C07D 453/02; A61K 31/475
[52] U.S. Cl. ............... 514/214; 514/216; 514/304; 514/305; 514/307; 514/310; 514/314; 514/341; 514/407; 540/582; 540/584; 540/585; 546/112; 546/124; 546/125; 546/126; 546/134; 546/136; 546/137; 546/139; 546/127; 546/129; 546/130; 546/133; 546/143; 546/146; 546/169; 546/279
[58] Field of Search ............... 546/124, 133, 125, 126, 546/128, 129, 130, 134, 136, 137, 139, 143, 146, 169, 279; 514/304, 305, 214, 216, 307, 314, 341, 407; 540/584, 585; 548/377

[56] References Cited

FOREIGN PATENT DOCUMENTS 0235878 9/1987 European Pat. Off. .
0255297 2/1988 European Pat. Off. .

OTHER PUBLICATIONS

Acta Pharm Suecica, 5, 71–76 (1968).
Ann. Pharm. Fr., 38 (4), 359–366 (1980).
Chem. Pharm. Bull. 20 (3), 476–486.
Acta Pharm. Suecica, 4, 211–16 (1967).
Acta Pharm. Suecica, 7, 239–246 (1972).
J. Pharm. Sci., 69 (6), 729–731 (1980).

*Primary Examiner*—Mary C. Lee
*Assistant Examiner*—Jacqueline Haley
*Attorney, Agent, or Firm*—George Tarnowski

[57] ABSTRACT

Aroyl ureas and carbamic acid derivatives of formula $$A-CO-NHCW-Y-B$$

and pharmaceutically acceptable salts thereof wherein
A is a specified aromatic radical including optionally substituted phenyl
W is O or S
Y is NH or S and
B is a specified saturated azacyclic ring, eg tropan-3-yl or quinuclidin-3-yl,
possess 5-HT₃-antagonistic activity and are, for example, useful in treatment of migraine, emesis, anxiety, gastro-intestinal disorders and as anti-psychotics.

11 Claims, No Drawings

HETEROCYCLIC COMPOUNDS USEFUL AS 5-HT$_3$ ANTAGONISTS

This application is a continuation-in-part of U.S. patent application Ser. No. 07/288732 filed Dec. 22, 1988 by Terence I. Ward and Janet C. White and entitled, as amended, Heterocyclic Compounds Useful as 5-HT$_3$ Antagonists, which is now abandoned.

This invention relates to heterocyclic compounds. In particular the invention relates to novel aryl or aroyl ureas or carbamic acid derivatives, and the corresponding thio analogues, to processes for their preparation, to their use and to pharmaceutical compositions containing them. The novel compounds of the invention are useful as antagonists of specific 5-hydroxytryptamine (5-HT) receptors as explained hereinbelow. Certain related aryl ureas and carbamic acid derivatives are disclosed in European Patent Application Nos. 235878 and 255297.

The novel heterocyclic compounds of the present invention are those of the general formula

A—X—NHCW—Y—B      (I)

and the pharmaceutically acceptable acid addition salts thereof. In this formula A represents an aromatic radical of the formula

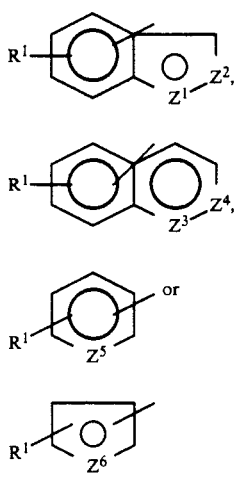

where the free valence is attached to either fused ring of formula (a) or (b),

R$^1$ represents hydrogen or one or more (e.g. 1 to 3) same or different substituents selected from lower alkyl, lower alkoxy [such as loweralkyloxy (e.g. methoxy, ethoxy, propoxy or butoxy), cyclo(-lower)alkyloxy, cyclo(lower)alkyl-loweralkyloxy (e.g. cyclopropylmethoxy), (lower)alkenyl(lower-)alkyloxy (e.g. allyloxy) and halo(lower)alkyloxy], hydroxy, halogen (e.g. chlorine), halo(lower)alkyl (e.g. trifluoromethyl), amino, nitro, carboxamido, phenyl(lower)alkyloxy (in which the phenyl group may be optionally substituted by one or more lower alkyl, loweralkyloxy or halo substituents), (lower)alkylamino, di(lower)alkylamino or acylamino [e.g. (lower) alkanoylamino or halo(lower) alkanoylamino]

Z$^1$-Z$^2$ represents CH$_2$—CH, NR$^2$—CH, O—CH, S—CH, CH$_2$—N, O—N, S—N, NR$^2$—N, CH—NR$^2$ or N—NR$^2$, [where R$^2$ is hydrogen, (lower)alkyl, or phenyl or phenyl(lower)alkyl in which the phenyl groups may optionally be substituted by one or more lower alkyl, lower alkyloxy or halo substituents]

Z$^3$-Z$^4$ represents CH=CH, O—CH$_2$ or N=CH

Z$^5$ represents N or CH

Z$^6$ represents O, S or NH

X represents a direct bond or CO,

W represents oxygen or sulphur,

Y represents NH or O,

B represents a saturated azacyclic ring of the formula

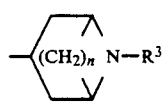

(II)

where n is 2,3 or 4 and R$^3$ is hydrogen, or (lower-)alkyl, or

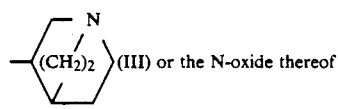

(III) or the N-oxide thereof or

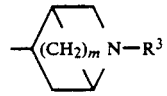

(IV)

where m is 1, 2 or 3 and R$^3$ has the meaning given above or

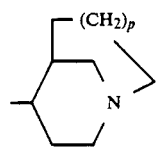

(V)

where p is 0, 1 or 2 or

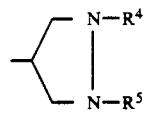

(VI)

where R$^4$ and R$^5$ are each hydrogen or lower alkyl with the proviso that when X is a direct bond, A represents a group of formula (c) or (d) and W represents oxygen, then the ring (c) or (d) does not contain a substituent ortho to the —X—NHCW—Y—B side chain.

The term "lower" as used herein means that the radical referred to contains up to 6 carbon atoms. The radical preferably contains up to 4 carbon atoms. For example, a lower alkyl group may be straight chain or branched and may be methyl, ethyl, propyl or butyl.

Preferably X represents CO.

When A represents a radical of formula (c) above, the radical preferably has the formula

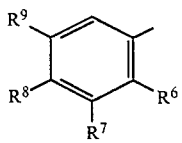

where $R^6$ to $R^9$ are independently hydrogen or a substituent $R^1$ as defined above. Particularly preferred meanings are those in which $R^6$ is lower alkoxy (e.g. methoxy) and $R^7$, $R^8$ and $R^9$ are hydrogen and those in which $R^6$ is lower alkyloxy (e.g. methoxy) or cyclo(-lower)alkyl(lower)alkyloxy (e.g. cyclopropylmethoxy), $R^7$ is hydrogen, $R^8$ is amino or lower alkylamino and $R^9$ is halo (e.g. chloro). Other preferred meanings are those in which $R^7$ and $R^9$ are chloro and $R^6$ and $R^8$ are hydrogen.

In the radical B of formula (II), preferably n is 2 and $R^3$ is lower-alkyl, preferably methyl. The radical in which n is 2 and $R^3$ is methyl is known as tropan-3-yl, otherwise 8-methyl-8-azabicyclo[3.2.1]octan-3-yl.

The radical of formula (III) is known as quinuclidinyl, otherwise 1-azabicyclo[2.2.2]octan-3-yl.

In the radical of formula (IV), preferably m is 2, and $R^3$ is preferably $C_{1-4}$-alkyl, particularly methyl.

In the radical of formula (V), p is preferably 1.

The compounds of the invention may contain one or more asymmetric carbon atoms so that the compounds can exist in different stereoisomeric forms. The compounds can, for example, exist as racemates or optically active forms. The optically active forms can be obtained by resolution of the racemates or by using an optically active form of the starting material in the processes described hereinafter. Furthermore radicals such as those of formulae (II) and (IV) can exist in two different configurations corresponding to the endo configuration as in tropine and the exo configuration as in pseudotropine. The endo configuration is preferred.

The compounds of the invention are aryl or aroyl ureas or carbamic acid derivatives (or their corresponding thio analogues) and may be prepared by methods known for the preparations of urea and carbamic acid derivatives (and thio analogues).

A first general process for preparing the compounds of the invention comprises reacting an isocyanate or isothiocyanate of formula (VII)

A—X—NCW (VII)

(where A, W and X are as defined above) with an amine or alcohol of formula (VIII)

B—YH (VIII)

(where B and Y are as defined above).

Such a reaction may, for example, be effected at room temperature in an organic solvent.

Compounds of the invention in which Y represents NH may be prepared by an alternative process in which a compound of general formula (IX)

A—X—NHCWNH₂ (IX)

(where A, W and X are as defined above) is reacted with an amine of general formula

B—NH₂ (X)

(where B is as defined above). This process may be performed in the absence of a solvent but is usually carried out by heating the reactants in the presence of a suitable inert organic solvent, for example toluene, pyridine, xylene, chlorobenzene, dimethylformamide or dioxan. Pyridine is the preferred solvent. Often it is convenient to reflux the reactants in the solvent.

Compounds of the invention in which X represents CO may be prepared by acylating a compound of formula

NH₂CWY—B (XI)

(where Y, W and B are as defined above) with an acylating agent containing the group A—CO— (where A is as defined above). Examples of acylating agents are reactive derivatives of acids of formula ACOOH such as the acid halides (e.g. the acid chloride) and the anhydride.

Compounds of the invention in which X represents a direct bond and Y is NH may be prepared by reacting an isocyanate or isothiocyanate of formula

B—NCW (XII)

(where B and W are as defined above) with an amine of formula

A—NH₂ (XIII)

(where A is as defined above).

The compounds of the invention in which B represents the N-oxide of the radical (III) may be prepared by oxidising a compound in which B represents the radical (III) with, for example, hydrogen peroxide or a peracid.

If in any of the above processes a reactant contains groups that would be affected under the reaction conditions employed for the reaction the group may be protected and the protecting group subsequently removed.

The starting materials for the above processes are either described in the literature or may be prepared by methods known for analogous compounds.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the present invention possess pharmacological activity. In particular they antagonise specific 5-hydroxytryptamine (5-HT) receptors in warm blooded animals. Specifically the compounds possess 5-HT₃ antagonistic activity and hence are of value in conditions where antagonism of 5-HT₃ receptors is desirable. 5-HT₃-antagonists are also termed "antagonists of "neuronal" 5-hydroxytryptamine receptors" and "serotonin (5-hydroxytryptamine) M-receptor antagonists". Such compounds have been described as being useful inter alia in the treatment of migraine, emesis, anxiety, gastrointestinal disorders and as antipsychotics.

The compounds of the invention are tested for 5-HT$_3$ antagonistic activity in the isolated right atrium of the rabbit heart based upon the method of Fozard J. R., Naunyn-Schmiedeberg's Arch. Pharmacol., 1984, 326, 36–44. This procedure relies upon the ability of 5-HT to stimulate 5-HT$_3$ receptors present on sympathetic nerve terminals in the heart, causing release of noradrenaline which evokes an increase in the spontaneous rate of beating. The antagonist potency is expressed as -log IC$_{50}$ (where IC$_{50}$ is the chronotropic response to $10^{-5}$M 5-HT by 50%)

When tested by this procedure N-(1-azabicyclo[2.2.2]-octan-3-yl)-N'-(3,5-dichlorophenyl)urea and N-[[[1-azabicyclo[2.2.2]octan-3-yl]amino]carbonyl]-2-methoxybenzamide representative compounds of this invention, had, respectively, -log IC$_{50}$ of 8.3 and 8.67. The (S)-enantiomer of the former compound had -log IC$_{50}$ of 9.3.

The compounds of the invention are tested for potential anxiolytic activity by a test procedure measuring mouse exploratory activity in a two-compartment light-/dark box based upon the procedure of B Costall et al, Neuropharmacology, 1987, 26, 195–200 and J N Crawley et al, Pharmac. Biochem. Behav., 1980, 13, 167–170. The test involves observing groups of mice placed in an open topped box, one third of which is painted black and illuminated under a dim red light and partitioned from the remainder of the box which is painted white and brightly illuminated. Access between the two sections is via an opening in the centre of the partition. The groups of mice are treated with vehicle or test compound and various behavioural parameters of the animals are measured including the number of exploratory rearings made by the mice in each section and the number of times the mice cross lines marked on the floor of each section. For each treatment group the mean number of line crossings and rears in each section of the box are calculated. Differences between drug-treated groups and vehicle-treated controls are compared using Student's unpaired t-test. Standard anxiotic agents significantly increase locomotion and rearing in the light section. Test compounds are considered to be active if they induce a similar set of changes and, in particular, if they produce a significant (p<0.05) increase in rearing activity in the light section of the box. Results for compounds of the invention and a standard anxiolytic agent are given below:

| Compound (dose mg/kg s.c.) | % Change Relative to Controls | |
|---|---|---|
| | Line Crossings | Rears |
| Ex. 1 (0.1) | +40%** | +85%* |
| Ex. 5 (0.1) | +20% | +73%* |
| Ex. 12 (1.0) | +42%* | +75%*** |
| Ex. 13 (0.1) | +69%** | +90%** |
| Chlordiazepoxide (2.0) | +42%* | +77%** |

*P < 0.05
**P < 0.01
***P < 0.001
(Student's unpaired t-test relative to vehicle treated controls.)

The invention further provides a compound of formula (I) or a pharmaceutically acceptable acid addition salt thereof for use in antagonising 5-HT$_3$ receptors in a mammal.

In a further aspect the invention provides the use of a compound of the invention for the treatment of migraine, emesis, anxiety, gastro-intestinal disorders or psychotic disorders. The invention also provides a method for the treatment of migraine, emesis, anxiety, gastro-intestinal disorders or psychotic disorders which comprises administering to a warm blooded animal in need thereof, an effective amount of the compound of the invention.

For certain of the above mentioned conditions it is clear that the compounds may be used prophylactically as well as for the alleviation of acute symptoms. References herein to "treatment" or the like are to be understood to include such prophylactic treatment, as well as treatment of the acute conditions.

The anti-emetic properties of the compounds are particularly advantageous in the treatment of nausea and vomiting associated with cancer chemotherapeutic agents and radiation therapy. The compounds are therefore of use in the treatment of cancer by chemotherapeutic (cytotoxic or cytostatic agents such as cisplatin, doxorubicin and cyclophosphamide) as well as irradiation. Accordingly, the invention also provides a product containing a cancer chemotherapeutic agent and a compound of the invention as a combined preparation for simultaneous, separate or sequential use in cancer therapy.

In a further aspect the invention provides a pharmaceutical composition comprising a compound of the invention in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions include powders, granules, tablets, capsules (e.g. hard and soft gelatin capsules), suppositories and pessaries. A solid carrier can be, for example, one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise a compound of the invention in a liquid carrier; such compositions may be administered for example in the form of a spray or as drops. The liquid carrier may be water (which may contain further components to provide the desired isotonicity and viscosity of the composition). The composition may also contain additional excipients such as preservatives, surface active agents and the like. The compositions may be contained in a nasal applicator that enables the composition to be administered as drugs or as a spray. For administration from an aerosol container the composition should also include a propellant. Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquids. The unit dosage form can be, for example, a capsule or tablet itself, or it can be the appropriate number of any such compositions in package form.

The quantity of the active ingredient in unit dose of composition may be varied or adjusted from 0.5 mg or less to 750 mg or more, according to the particular need and the activity of the active ingredient.

The invention also includes the compounds in the absence of the carrier where the compounds are in unit dosage form.

The following Examples illustrate the invention.

EXAMPLE 1

N-(1-azabicyclo[2.2.2]octan-3-yl-N'-(3,5-dichlorophenyl)urea

A solution of 3,5-dichlorophenyl isocyanate (1.88 g, 10 mmol) in toluene (20 ml) was added at 0° to 1-azabicyclo[2.2.2]octan-3-amine (3-aminoquinuclidine) (1.26 g, 10 mmol) in THF (40 ml). The mixture was stirred at room temperature overnight and evaporated to dryness. The residue was partitioned between ether and dilute hydrochloric acid. The aqueous phase was basified with potassium carbonate and extracted with ethyl acetate. The dried (Na$_2$SO$_4$)ethyl acetate phase was evaporated and the residue (1.64 g) converted to the 1:1 oxalate, quarter hydrate, mp 208°–209° C. (dec).

EXAMPLE 2

N-[[[1-azabicyclo[2.2.2]octan-3-yl]amino]carbonyl]-3,5-dichlorobenzamide

3-Aminoquinuclidine (1.26 g, 10 mmol) and 3,5-dichlorobenzoylurea (2.2 g, 9.44 mmol) in pyridine (15 ml) were stirred and refluxed overnight under nitrogen, filtered hot and allowed to cool to room temperature. The precipitated solid was collected, washed with ethyl acetate and dried to give the title compound (0.93 g) which was converted to the hydrochloride, monohydrate mp 253°–254° C.

EXAMPLE 3

(Endo)-N-(3,5-dichlorobenzoyl)-O-(8-methyl-8-azabicyclo[3.2.1]oct-3-yl)carbamate Tropine (1 g, 7.09 mmol) was dissolved in dichloromethane (10 ml) then treated with 3,5-dichlorobenzoyl isocyanate (1.6 g, 7.34 mmol) in dichloromethane (8 ml) to give a clear solution, which was left overnight under nitrogen. Methanol was added, the solution was evaporated, and the residue triturated with ether to give product, 1.62 g. This was triturated in refluxing acetonitrile (40 ml) for about 30 mins, collected and dried to give 0.32 g, containing 1/6 mole acetonitrile mp 175°–177° C.

EXAMPLE 4

N-(3,5-dichlorophenyl)-N'-(1,2-diethylpyrazolidin-4-yl)urea.

A solution of 4-amino-1,2-diethylpyrazolidine (1.26 g, 8.8 mmol) in anhydrous toluene (5 ml) was added to a solution of 3,5-dichlorophenyl isocyanate (1.71 g, 9.1 mmol) in dry toluene (20 ml) and the mixture stirred overnight. The precipitated solid was collected, washed with toluene and dried to give the title compound, 1.94 g. This was converted to the 1:1 maleate, mp 165°–167° C.

EXAMPLE 5

N-[[[1-Azabicyclo[2.2.2]octan-3-yl]amino]carbonyl]-2-methoxybenzamide (a) 2-Methoxybenzoyl isocyanate 2-Methoxybenzamide (2.27 g, 15.04 mmol) and oxalyl chloride (2.4 g, 18.9 mmol) were heated together in 1,2-dichloroethane (40 ml) for 16 h at reflux. The resulting solution was concentrated under reduced pressure to a residue which was re-evaporated with toluene to give the crude acyl isocyanate as an oil (2.94 g).

(b) N-[[[1-Azabicyclo[2.2.2]octan-3-yl]amino]carbonyl]-2-methoxybenzamide

This compound was prepared by the procedure of example 1, using 3-aminoquinuclidine (0.63 g, 5 mmol) and 2-methoxybenzoyl isocyanate (1.0 g, 5 mmol), giving crude title product (1.6 g) which was purified as its 1:1 fumarate mp 187°–188° C. (0.79 g)

EXAMPLE 6

N-(Azabicyclo[2.2.2]octan-3-yl)-N'-(3,5-dichlorophenyl)thiourea

Thiophosgene (1.0 ml, 1.51 g, 13.13 mmol) was suspended in water (10 ml) and stirred vigorously while 3,5-dichloroaniline (1.62 g, 10 mmol) in chloroform (8 ml) was added over 1 min. Triethylamine (1.4 g, 13.86 mmol) was added and stirring was continued for 30 min.

The aqueous phase was discarded and the chloroform retained.

3-Aminoquinuclidine dihydrochloride (1.99 g, 10 mmol) was dissolved in water (2 ml) and treated with sodium hydroxide pellets until the pH was 9. This solution was then added to the above chloroform solution and the two stirred together overnight.

The aqueous phase was extracted 3 times with chloroform. The combined organic phases were washed once with water. An insoluble oil was separated. The chloroform solution was dried ($Na_2SO_4$) and evaporated, and the residue combined with the insoluble oil. This material was triturated with dichloromethane for 3 h to give the title product, 2.09 g, mp 137°–140° C., as hydrochloride containing 0.5 mole of dichloromethane not removable by drying.

EXAMPLE 7

Endo-N-(3,5-dichlorophenyl)-N'-(8-methyl-8-azabicyclo[3.2.1]octan-3-yl)urea

The above compound was prepared, following the procedure of Example 1, from 3,5-dichlorophenylisocyanate (0.94 g, 5 mmol) and (endo)-8-methyl-8-azabicyclo[3.2.1]octan-3-amine (3-aminotropane) (0.70 g, 5 mmol). The product was isolated as the 1:1 maleate (0.58 g), mp 208°–210° C.

EXAMPLE 8

N-(1-Azabicyclo[2.2.2]octan-3-yl)-N'-(3-trifluoromethylphenyl)urea

The above compound was prepared, following the procedure of Example 1, from 3-aminoquinuclidine (0.63 g, 5 mmol). and 3-trifluoromethylphenyl isocyanate (0.94 g, 5 mmol). The product was isolated as the hydrochloride (1.02 g), mp 245°–247° C.

EXAMPLE 9

N-(1-Azabicyclo[2.2.2]octan-3-yl)-N'-(4-chlorophenyl)urea

The above compound was prepared, following the procedure of Example 1, from 3-aminoquinuclidine (0.63 g, 5 mmol) and 4-chlorophenyl isocyanate (0.768 g, 5 mmol). The product was purified as the 1:1 maleate (1.23 g), mp 182°–183° C. (dec).

EXAMPLE 10

N-(1-Azabicyclo[2.2.2]octan-3-yl)-N'-(1-methyl-1H-indol-3-yl)urea

The above compound was prepared, following the procedure of Example 1, from 3-aminoquinuclidine (0.96 g, 7.62 mmol) and 1-methyl-3-isocyanatoindole (prepared from 1.5 g, 7.5 mmol), 1-methylindole-3-carbonyl azide which was prepared by reacting 1-methylindole-3-carboxylic acid with diphenylphosphoryl azide). The product was isolated as the 1:1 oxalate (0.32 g), one-third 2-propanol, mp (double) 120°–124° C., 130°–132° C.

EXAMPLE 11

N-(1-Azabicyclo[2.2.2]octan-3-yl)-N'-(2-benzothienyl)urea

The above compound was prepared, following the procedure of Example 1, from 3-aminoquinuclidine (0.53 g, 4.21 mmol) and 2-isocyanatobenzothiophene (0.73 g, 4.17 mmol). The product was isolated as the 1:1 oxalate (0.18 g), quarter hydrate, mp 204°–206° C.

EXAMPLE 12

(S)-(−)-N-(1-Azabicyclo[2.2.2]octan-3-yl)-N'-(3,5-dichlorophenyl)urea (a) (3S)-3-[(S)-α-methylbenzylamino]quinuclidine A mixture of 3-quinuclidinone hydrochloride (80.5 g, 0.5 mol), (S)-α-methylbenzylamine (180 g, 1.49 mol), sodium cyanoborohydride (31 g, 0.5 mol). 3Å molecular sieve (75 g), methanol (750 ml), and enough gaseous hydrogen chloride to give a pH of approx 6 was stirred in ice for 1 h, then at room temperature overnight, with addition of hydrogen chloride as necessary to maintain pH 6. The mixture was filtered and the filtrate evaporated. The residue was dissolved in water, basified with potassium hydroxide, and extracted with ethyl acetate. The ethyl acetate extracts were dried ($Na_2SO_4$), evaporated and distilled. The product fraction, bp 138°–142° C. (2 mbar) was fractionally crystallised as its hydrochloride to give the title compound (29.22 g), mp 238°–242° C. (phase change 193°–200° C.).

(b) (S)-(−)-3-aminoquinuclidine (3S)-3-[(S)-α-methylbenzylamino]quinuclidine hydrochloride (24.38 g, 91.5 mmol) in water (80 ml) and glacial acetic acid (130 ml) was hydrogenated over 10% Pd/C (1.2 g) at 50° C. and 40 psi (about $2.7 \times 10^5$ Pa). The mixture was filtered, the filtrate treated with concentrated hydrochloric acid (10 ml) and evaporated. The residue was triturated with isopropanol to give the title compound dihydrochloride (16.6 g). A second crop (0.5 g) of dihydrobromide salt, mp 273°–280° C. (phase change >240° C.) $[\alpha]_D^{25} = -16°(C=1, H_2O)$ was obtained from the isopropanol mother-liquors by treating with excess hydrogen bromide and concentrating to low volume until crystallisation occurred.

(c) (S)-(−)-N-(1-Azabicyclo[2.2.2]octan-3-yl)-N'-(3,5-dichlorophenyl)urea

The above compound was prepared, following the procedure of Example 1, from (S)-3-aminoquinuclidine (1.98 g, 15.71 mmol) and 3,5-dichlorophenyl isocyanate (2.96 g, 15.74 mmol) to give the title compound (0.95 g), mp 200°–201° C., $[\alpha]_D^{26} = -21°(C=1, CHCl_3)$.

EXAMPLE 13

(R)-(+)-N-(1-Azabicyclo[2.2.2]octan-3-yl)-N'-(3,5-dichlorophenyl)urea (a) (3R)-3-[(S)-α-methylbenzylamino]quinuclidine The above compound was obtained from the mother-liquors of the (3S)-3-[(S)-α-methylbenzylamino]quinuclidine hydrochloride, the preparation of which is given in example 12a, by fractional crystallisation as the 1:1 di-p-toluoyl-L-tartrate (44.8 g), mp 172°–174° C.

(b) (R)-(+)-3-aminoquinuclidine (3R)-3-[(S)-α-methylbenzylamino]quinuclidine di-p-toluoyl-L-tartrate (39.7 g, 62.6 mmol) was partitioned between ether (200 ml) and 5M aqueous potassium hydroxide (50 ml). The aqueous phase was extracted again with ether, the combined ethereal phases dried ($Na_2SO_4$) and evaporated. The residue was hydrogenated in glacial acetic acid (130 ml) over 10% Pd/C (1.1 g) at 50° C. and 45 psi (about $3.1 \times 10^5$ Pa). The mixture was worked-up as in example 12b to give the title compound dihydrochloride (10.1 g), $[\alpha]_D^{25} = +16.5 (C=1, H_2O)$ with a second crop of dihydrobromide (0.5 g), mp 284°–285° C. (phase change >230° C.).

(c) (R)-(+)-N-(1-Azabicyclo[2.2.2]octan-3-yl)-N-(3,5-dichlorophenyl)urea

The above compound was prepared, following the procedure of Example 1, from (R)-3-aminoquinuclidine (1.26 g, 10 mmol) and 3,5-dichlorophenyl isocyanate (1.88 g, 10 mmol) to give the title compound quarter hydrate (1.35 g), mp 190°–194° C. (forms a gum at 180°–183° C.), $[\alpha]_D^{23} = +23°$ (C=1, CHCl$_3$).

EXAMPLE 14

N-[[[1-Azabicyclo[2.2.2]octan-3-yl]amino]carbonyl]-3-trifluoromethylbenzamide (a) N-Trifluoromethylbenzoylurea A mixture of 3-trifluoromethylbenzoic acid (10 g, 52.6 mmol) and thionyl chloride (15 ml) was heated under reflux for 0.75 h. The excess thionyl chloride was evaporated, urea (10 g, 167 mmol) was added to the residue, and the mixture heated at 100°–110° C. for 1.5 h. The solid was extracted under reflux with water (20 ml), cooled, basified with sodium bicarbonate, the solid collected and recrystallised from aqueous acetic acid to give product (8 g), mp 191°–193° C.

(b) N-[[[1-azabicyclo[2.2.2]octan-3-yl]amino]carbonyl]-3-trifluoromethylbenzamide The above compound was prepared from 3-amino quinuclidine dihydrochloride (1.0 g, 5 mmol), 3-trifluoromethylbenzoylurea (1.16 g, 5 mmol) and diisopropylethylamine (1.29 g, 10 mmol) in pyridine (20 ml), by refluxing under nitrogen overnight. The solvent was evaporated and the residue worked-up as in Example 1. The product (1.18 g) was converted to oxalate salt, mp 197°–200° C.

EXAMPLE 15

N-[[[1-azabicyclo[2.2.2]octan-3-yl]amino]carbonyl]-4-methoxybenzamide

The above compound was prepared, following the procedure of Example 14b, from 3-aminoquinuclidine dihydrochloride (1.0 g, 5 mmol), 4-methoxybenzoylurea (0.97 g, 5 mmol) and di-isopropylethylamine (1.29 g, 10 mmol) in pyridine (20 ml). The product (1.12 g) was converted to 1:1 maleate half hydrate, mp 166°–168° C.

EXAMPLE 16

N-[[[1-Azabicyclo[2.2.2]octan-3-yl]amino]carbonyl]-naphthalene-2-carboxamide (a) 2-Naphthoylurea The above compound was prepared, following the procedure of Example 14a from 2-napthoic acid (8.2 g, 47.7 mmol), thionyl chloride (40 ml) and urea (10 g, 167 mmol) to give the title compound (7.1 g), mp 207°–208° C.

(b) N-[[[1-Azabicyclo[2.2.2]octan-3-yl]amino]carbonyl]naphthalene-2-carboxamide

The above compound was prepared, following the procedure of Example 14b, from 3-aminoquinuclidine dihydrochloride (1.0 g, 5 mmol), 2-naphthoylurea (1.07 g, 5 mmol) and di-isopropylethylamine (1.29 g, 5 mmol) in pyridine (20 ml). The title compound was isolated as hydrochloride half hydrate (1.39 g), mp 271°–273° C. (dec).

EXAMPLE 17

N-[[[1-Azabicyclo[2.2.2]octan-3-yl]amino]carbonyl]-2-furancarboxamide

The above compound was prepared, following the procedure of Example 14b, from 3-aminoquinuclidine dihydrochloride (1.0 g, 5 mmol), 2-furoylurea (0.77 g, 5 mmol), and diisopropylethylamine (1.3 g, 10 mmol) in pyridine (20 ml). The product (0.58 g) was converted to the 1:1 succinate mp 156°–159° C.

EXAMPLE 18

N-[[[1-Azabicyclo[2.2.2]octan-3-yl]amino]carbonyl]-2,6-dimethylbenzamide (a) 2,6-Dimethylbenzoylurea The above compound was prepared, following the procedure of Example 14a, from 2,6-dimethylbenzoic acid (10 g, 66.7 mmol), thionyl chloride (15 ml) and urea (10 g, 168 mmol) to give the title compound (8.9 g), mp 210°–213° C.

(b) N-[[[1-Azabicyclo[2.2.2]octan-3-yl]amino]carbonyl]-2,6-dimethylbenzamide

The above compound was prepared, following the procedure of Example 14b, from 3-aminoquinuclidine dihydrochloride (1.0 g, 5 mmol), 2,6-dimethylbenzoylurea (0.96 g, 5 mmol) and diisopropylethylamine (1.3 g, 10 mmol) in pyridine (20 ml) by refluxing for 4 days. The product was recrystallised from acetonitrile to give the title compound quarter hydrate (0.54 g), mp 230°–231° C.

EXAMPLE 19

N-[[[1-Azabicyclo[2.2.2]octan-3-yl]amino]carbonyl]-2-thiophenecarboxamide

The above compound was prepared, following the procedure of Example 14b, from 3-aminoquinuclidine dihydrochloride (1.0 g, 5 mmol), 2-thienoylurea (0.85 g, 5 mmol) and diisopropylethylamine (1.3 g, 10 mmol) in pyridine (20 ml). The product (0.79 g) was converted to hydrochloride half hydrate, mp 232°–233° C.

EXAMPLE 20

N-[[[1-Azabicyclo[2.2.2]octan-3-yl]amino]carbonyl]-2-fluorobenzamide (a) 2-Fluorobenzoyl isocyanate The above compound was prepared, following the procedure of Example 5a, from 2-fluorobenzamide (0.97 g, 6.98 mmol) and oxalyl chloride (1.08 g, 8.36 mmol) in 1,2-dichloroethane (20 ml) to give crude product (1.3 g).

(b) N-[[[1-Azabicyclo[2.2.2]octan-3-yl]amino]carbonyl]-2-fluorobenzamide

The above compound was prepared, following the procedure of Example 1, from 3-aminoquinuclidine (0.63 g, 5 mmol) and crude 2-fluorobenzoyl isocyanate (1.3 g, ca 7 mmol). The product (1.35 g) was converted to the 1:1 succinate, mp 187°–188° C.

EXAMPLE 21

N-[[[1-Azabicyclo[2.2.2]octan-3-yl]amino]carbonyl]-2-ethoxybenzamide (a) 2-Ethoxybenzoyl isocyanate The above compound was prepared, following the procedure of Example 5a, from 2-ethoxybenzamide (1.15 g, 6.97 mmol) and oxalyl chloride (1.08 g, 8.36 mmol) in 1,2-dichloroethane (20 ml) to give crude product (1.59 g).

(b) N-[[[1-Azabicyclo[2.2.2]octan-3-yl]amino]carbonyl]-2-ethoxybenzamide

The above compound was prepared, following the procedure of Example 1, from 3-aminoquinuclidine (0.63 g, 5 mmol) and crude 2-ethoxybenzoyl isocyanate (1.59 g, ca 7 mmol). The product (1.77 g) was converted to the 1:1 fumarate, mp 198°–199° C.

EXAMPLE 22

N-[[[1-Azabicyclo[2.2.2]octan-3-yl] amino]carbonyl]-2-isopropoxybenzamide (a) 2-Isopropoxybenzoyl isocyanate
The above compound was prepared, following the procedure of Example 5a, from 2-isopropoxybenzamide (0.44 g, 2.46 mmol) and oxalyl chloride (0.38 g, 2.97 mmol) in 1,2-dichloroethane (10 ml) to give crude product (0.58 g).

(b) N-[[[1-Azabicyclo[2.2.2]octan-3-yl] amino]carbonyl]-2-isopropoxybenzamide
The above compound was prepared, following the procedure of Example 1, from 3-aminoquinculidine (0.31 g, 2.46 mmol) and crude 2-isopropoxybenzoyl isocyanate (0.58 g, ca 2.5 mmol). The product (0.51 g) was converted to the 1:1 fumarate, mp 171°–175° C.

EXAMPLE 23

2-Allyloxy-N-[[[1-Azabicyclo[2.2.2] octan-3-yl]amino]carbonyl]benzamide (a) 2-Allyloxybenzoyl isocyanate
The above compound was prepared, following the procedure of Example 5a, from 2-allyloxybenzamide (0.39 g, 2.2 mmol) an oxalyl chloride (0.35 g, 2.74 mmol) in 1.2 -dichloroethane (10 ml) to give crude product (0.53 g).

(b) 2-Allyloxy-N-[[[1-Azabicyclo[2.2.2]octan-3-yl]amino]carbonyl]benzamide
The above compound was prepared, following the procedure of Example 1, from 3-aminoquinuclidine (0.28 g, 2.2 mmol) and 2-allyloxybenzoyl isocyanate (0.53 g, ca 2.2 mmol). The product (0.61 g) was converted to the 1:1 fumarate.

EXAMPLE 24

N-[[[1-Azabicyclo[2.2.2]octane-3-yl] amino]carbonyl]-2-pyridinecarboxamide (a) 2-Pyridoylurea
A mixture of sodium (0.23 g, 10 mmol), urea (0.8 g, 13.3 mmol) and liquid ammonia (40 ml) was stirred until the blue colour was discharged, then ethyl 2-pyridinecarboxylic acid (2.85 g, 18.8 mmol) was added all at once. After 1 h the ammonia was evaporated and the residue triturated with water to give the above compound, mp 183°–185° C.

(b) N-[[[1-Azabicyclo[2.2.2]-3yl]amino] carbonyl]-2-pyridinecarboxamide
The above compound was prepared, following the procedure of Example 14b, from 3-aminoquinuclidine dihydrochloride(1.0 g, 5 mmol), 2-pyridoylurea (0.82 g, 5 mmol) and di-isopropylethylamine (1.3 g, 10 mmol) in pyridine (20 ml) by refluxing for 4 days. The pyridine was evaporated and the residue partitioned between ether and 10% aqueous w/v citric acid. The mixture was filtered, the aqueous phase washed with ether, then basified with potassium carbonate to precipitate the title compound (0.60 g) which was converted to the 1:1 fumarate, mp 202°–203° C.

EXAMPLE 25

Endo-N-[[[8-methyl-8azabicyclo[3.2.1]octan-3-yl] amino]carbonyl]-2-methoxybenzamide The above compound was prepared, following the procedure of Example 1, from endo-3-aminotropane (0.70 g, 5 mmol) and 2-methoxybenzoyl isocyanate (1.0 g, 5 mmol). The product (2.1 g, crude) was converted to hydrochloride (0.65 g).

EXAMPLE 26

N-[[[1-Azabicyclo[2.2.2]octan-3-yl] amino]carbonyl]-2-methylbenzamide (a) 2-Methylbenzoyl isocyanate
The above compound was prepared, following the procedure of Example 5a, from 2-methylbenzamide (0.95 g, 7 mmol) and oxalyl chloride (1.08 g, 8.36 mmol) in 1,2-dichloroethane (20 ml) to give crude product (1.35 g).

(b) N-[[[1-Azabicyclo[2.2.2]octan-3-yl] amino]carbonyl]-2-methylbenzamide
The above compound was prepared, following the procedure of Example 1, from 3-aminoquinuclidine (0.63 g, 5 mmol) and crude 2-methylbenzoyl isocyanate (1.35 g, ca 7 mmol). The product (1.23 g) was converted to the 1:1 fumarate, mp 216°–217° C.

EXAMPLE 27

N-[[[1-Azabicyclo[2.2.2]octan-3-yl] amino]carbonyl]2-((cyclproppyl)methoxy)benzamide (a) 2-((Cyclopropyl)methoxy)benzamide
2-Hydroxybenzamide (5.17 g, 37.74 mmol) and sodium hydroxide (1.5 g, 37.5 mmol) in ethanol (20 ml) were refluxed for 1 h to give a clear solution. (Bromomethyl)cyclopropane (5.09 g, 37.7 mmol) was added and the mixture refluxed for 36 h. The solvent was evaporated and the residue triturated thoroughly with ether and water to give the above compound (4.37 g).

(b) 2-((Cyclopropyl)methoxy)benzoyl isocyanate
The above compound was prepared, following the procedures of Example 5a, from 2-((cyclopropyl)methoxy)benzamide (0.95 g, 5 mmol) and oxalyl chloride (0.79 g, 6.2 mmol) in 1,2-dichloroethane (20 ml) to give the crude product (1.4 g).

(c) N-[[[1-Azabicyclo[2.2.2]octan-3-yl] amino]carbonyl]-2-((cyclopropyl)methoxy)benzamide
The above compound was prepared, following the procedure of Example 1, from 3-aminoquinuclidine (0.63 g, 5 mmol) and crude 2-((cyclopropyl)methoxy)-benzamide (1.4 g, ca 5 mmol). The product was converted to the 1:1 oxalate, half hydrate mp 128°–131° C.

EXAMPLE 28

(S)-N-[[[1-Azabicyclo[2.2.2]octan-3-yl] amino]carbonyl]-2-methoxybenzamide

The above compound was prepared, following the procedure of Example 1, from (S)-3-aminoquinuclidine (0.63 g, 5 mmol) and 2-methoxybenzoyl isocyanate (1.26 g, 7 mmol). The product (1.44 g) was converted to the 1:1 fumarate, mp 158°–159° C. (dec).

EXAMPLE 29

(R)-N-[[[1-Azabicyclo[2.2.2]octan-3-yl] amino]carbonyl]-2-methoxybenzamide

The above compound was prepared, following the procedure of Example 1, from (R)-3-aminoquinuclidine (0.63 g, 5 mmol) and 2-methoxybenzoyl isocyanate (1.33 g, 7.5 mmol). The product (1.49 g) was converted to the 1:1 fumarate, mp 158°–159° C. (dec).

EXAMPLE 30

(Endo)-O-[8-Methyl-8-azabicyclo[3.2.1]octan-3-yl]N-(3,5-dichlorophenyl)carbamate Tropine (1.0 g, 7.04 mmol) was added to 3,5-dichlorophenyl isocyanate (1.32 g, 7.02 mmol) in dichloromethane (20 ml) at room temperature under nitrogen. The reaction mixture was stirred for 20 h, the solid collected and partitioned between ether and dilute hydrochloric acid. The insoluble solid was collected and washed with dilute hydrochloric acid then ether to give the above compound as its hydrochloride (0.73 g), mp 288°–294° C. (dec).

EXAMPLE 31 endo-N-[[(8-Methyl-8-azabicyclo[3.2.1]octan-3-yl)amino]carbonyl]-2-cyclopropylmethoxy)benzamide (a) Salicylamide (15.22 g), potassium hydroxide (85%, 7.73 g) and cyclopropylmethyl bromide (16.024 g) were heated together under reflux in absolute ethanol (100 ml) for 9½ hours. The cooled mixture was filtered to remove inorganic products and the filtrate was evaporated to an oil. The oil was dissolved in 1:1 toluene-:ethyl acetate (200 ml) and the solution was washed with 10% potassium hydroxide solution (2×30 ml), water (50 ml) and saturated brine (50 ml), dried (Na$_2$SO$_4$), and concentrated under reduced pressure, leaving 2-(cyclopropylmethoxy)benzamide as an oil which crystallised (17.606 g, 83%), mp 95°–100° C.

(b) 2-(Cyclopropylmethoxy)benzamide [from part (a) above: 17.4 g], oxalyl chloride (12.1 ml) and 1,2-dichloroethane (190 ml) were heated together at 80° C. for 19 hours. The cooled solution was concentrated under reduced pressure to an oil which was re-evaporated with toluene (2×150 ml) to remove residual oxalyl chloride. The residual crude 2-(cyclopropylmethoxy)benzoyl isocyanate was dissolved in dry THF (230 ml).

This solution (220 ml) was added by cannula under argon to an ice-cold solution of endo-3-aminotropane (11.5 g) in dry THF (660 ml). The mixture was allowed to warm to room temperature overnight under argon and was then quenched with methanol (100 ml), stirred 3 hours, and evaporated to an oil under reduced pressure.

This oil was partitioned between 6N hydrochloric acid (200 ml) and ether (3×100 ml). The acid phase was made basic to pH 10 with sodium hydroxide and ice cooling, and the precipitated base was extracted into chloroform (5×100 ml). The extracts were dried (Na$_2$SO$_4$) and evaporated, leaving an oil which crystallised spontaneously (25.5 g, 88%).

The base was converted to its 1:1 maleic acid salt in propan-2-ol and crystallised twice from this solvent with charcoal treatment, giving the title salt as its 1:1 maleic acid salt (24.91 g), m.p. 162°–164° C.

Found: C, 60.91; H, 6.66; N, 8.83. C$_{20}$H$_{27}$N$_3$O$_3$.C$_4$H$_4$O$_4$ requires C, 60.88; H, 6.60; N, 8.87%.

We claim:

1. A heterocyclic compound of the general formula

A—CONHCW—Y—B    (I)

or a pharmaceutically acceptable acid addition salt thereof where

A represents an aromatic radical of the formula

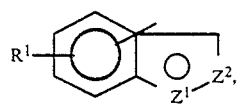

(a)

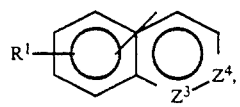

(b)

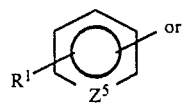

(c)

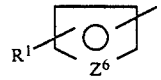

(d)

R$^1$ represents hydrogen or one or more same or different substituents selected from lower alkyl, loweralkyloxy, cyclo(lower)alkyloxy, cyclo(lower)alkyl-loweralkyloxy, (lower)alkenyl(lower)alkyloxy, halo(lower)alkyloxy, hydroxy, halogen, halo(lower)alkyl, amino, nitro, carboxamido, phenyl(lower)alkyloxy (in which the phenyl group may be optionally substituted by one or more lower alkyl, loweralkyloxy or halo substituents), (lower)alkylamino, di(lower)alkylamino or acylamino Z$^1$-Z$^2$ represents CH$_2$—CH, NR$^2$—CH, O—CH, S—CH, CH$_2$—N, O—N, S—N, NR$^2$—N, CH—NR$^2$, or N—NR$^2$, [where R$^2$ is hydrogen, (lower)alkyl or phenyl or phenyl(lower)alkyl in which the phenyl groups may optionally be substituted by one or more lower alkyl, lower alkyloxy or halo substituents]

Z$^3$-Z$^4$ represents CH=CH, O—CH$_2$ or N=CH

Z$_5$ represents N or CH

Z$^6$ represents O, S or NH

W represents oxygen or sulphur

Y represents NH or O

B represents a saturated azacyclic ring of the formula

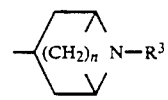

(II)

where n is 2,3 or 4 and R$^3$ is hydrogen, or (lower)alkyl or

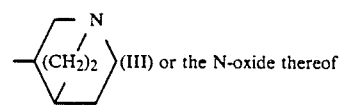

(III) or the N-oxide thereof or

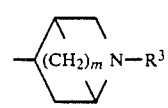

(IV)

where m is 1, 2 or 3 or R³ has the meaning given above or

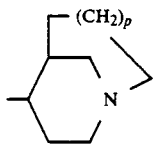   (V)

where p is 0, 1 or 2

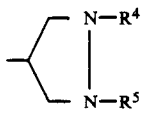   (VI)

where R⁴ and R⁵ are each hydrogen or lower alkyl.

2. A compound as claimed in claim 1 in which A is of the formula

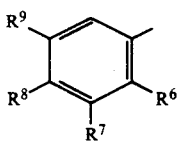   (XIV)

where $R^6$ to $R^9$ are independently hydrogen or a substituent $R^1$ as defined in claim 1.

3. A compound as claimed in claim 2 which $R^6$ is lower alkyloxy and $R^7$, $R^8$ and $R^9$ are hydrogen or $R^6$ is lower alkyloxy or cyclo(lower)alkyl(lower)alkyloxy, $R^7$ is hydrogen, $R^8$ is amino or loweralkylamino and $R^9$ is halo or $R^7$ and $R^9$ are chloro and $R^6$ and $R^8$ are hydrogen.

4. A compound as claimed in claim 1, 2 or 3 wherein B is tropan-3-yl or quinuclidin-3-yl.

5. A compound as claimed in claim 1 in which A represents a radical of formula (a) or (b) where $R^1$ is hydrogen or a single halo(lower)alkyl, lower alkyloxy, lower alkyl, amino, (lower)alkylamino, di(lower)alkylamino or (lower)alkanoylamino substituent or A represents a radical of formula (c) in which $Z^5$ represents CH and $R^1$ represents hydrogen or one or more same or different substituents selected from lower alkyl, lower alkyloxy, hydroxy, halogen, halo(lower)alkyl, amino, nitro, carboxamido(lower)alkylamino, di(lower)alkylamino or (lower)alkanoylamino.

6. A compound as claimed in claim 1 which is N-[[[1-azabicyclo[2.2.2]octan-3-yl]amino]carbonyl]-2-methoxybenzamide or a pharmaceutically acceptable salt thereof.

7. A compound as claimed in claim 1 which is N-[[[1-azabicyclo[2.2.2]octan-3-yl]amino]carbonyl]3,5-dichlorobenzamide, (endo)-N-(3,5-dichlorobenzoyl)-O-(8-methyl-8-azabicyclo[3.2.1]oct-3-yl)carbamate or a pharmaceutically acceptable salt thereof.

8. A compound as claimed in claim 1 which is N-[[[1-azabicyclo[2.2.2]octan-3-yl]amino]carbonyl]-3-trifluoromethylbenzamide. N-[[[1-azabicyclo[2.2.2]octan-3-yl]amino]carbonyl]-4-methoxybenzamide or N-[[[1-azabicyclo[2.2.2]octan-3-yl]amino]carbonyl]naphthalene-2-carboxamide or a pharmaceutically acceptable salt thereof.

9. A compound as claimed in claim 1 which is N-[[[1-azabicyclo[2.2.2]octan-3-yl]amino]carbonyl]-2-furancarboxamide, N-[[[1-azabicyclo[2.2.2]octan-3-yl]amino]carbonyl]-2,6-dimethylbenzamide, N-[[[1-azabicyclo[2.2.2]octan-3-yl]amino]carbonyl]-2-thiophenecarboxamide, N-[[[1-azabicyclo[2.2.2]octan-3-yl]amino]carbonyl]-2-fluorobenzamide, N-[[[1-azabicyclo[2.2.2]octan-3-yl]amino]carbonyl]-2-ethyoxybenzamide, N-[[[1-azabicyclo[2.2.2octan-3-yl]amino]carbonyl]-2-isoproxybenzamide, 2-allyloxy-N-[[[1-azabicyclo[2.2.2]octan-3-yl]amino]carbonyl]benzamide, N-[[[1-azabicyclo[2.2.2]octan-3-yl]amino]carbonyl]-2-pyridinecarboxamide, (endo)-N-[[[8-methyl-8-azabicyclo[3.2.1]octan-3-yl]amino]carbonyl]-2-methoxybenzamide, N[[[1-azabicyclo[2.2.2]octan-3-yl]amino]carbonyl]-2-methylbenzamide, N-[[[1-azabicyclo[2.2.2]octan-3-yl]amino]carbonyl]-2-((cyclopropyl)methoxy)-benzamide, (S)-N-[[[1-azabicyclo[2.2.2]octan-3-yl]amino]carbonyl]2-methoxybenzamide, (R)-N-[[[1-azabicyclo[2.2.2]-octan-3-yl]amino]carbonyl]2-methoxybenzamide or a pharmaceutically acceptable salt thereof.

10. A compound as claimed in claim 1 which is endo-N-[[(8-methyl-8-azabicyclo[3.2.1]octan-3-yl)amino]carbonyl]-2-(cyclopropylmethoxy)benzamide or a pharmaceutically acceptable salt thereof.

11. A method for the treatment of migraine, emesis, anxiety, gastro-intestinal disorders or psychotic disorders which comprises administering to a warm blooded animal in need thereof, an effective amount of a heterocyclic compound of the formula

A—CONHCW—Y—B   (I)

or a pharmaceutically acceptable acid addition salt thereof where
A represents an aromatic radical of the formula

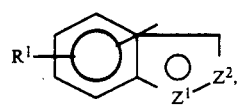   (a)

   (b)

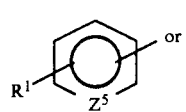   (c)

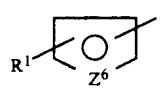   (d)

[where the free valence is attached to either fused ring of formula (a) or (b)]

$R^1$ represents hydrogen or one or more same or different substituents selected from lower alkyl, loweralkyloxy, cyclo(lower)alkyloxy, cyclo(lower)alkyl-loweralkyloxy, (lower)alkenyl(lower)alkyloxy, halo(lower)alkyloxy, hydroxy, halogen, halo(lower) alkyl, amino, nitro, carboxamido, phenyl(lower)alkyloxy (in which the phenyl group may be optionally substituted by one or more lower alkyl, loweralkyloxy or halo substituents), (lower)alkylamino, di(lower)alkylamino or acylamino $Z^1$-$Z^2$ represents CH₂—CH, NR²—CH, O—CH, S—CH, CH₂—N, O—N, S—N, NR²—N, CH—NR² or N—NR², (where R² is hydrogen, (lower)alkyl or phenyl, or phenyl(lower) alkyl in which the phenyl groups may optionally be substituted by one or more lower alkyl, lower alkyloxy or halo substituents)

$Z^3$-$Z^4$ represents CH=CH, O—CH₂ or N=CH $Z^5$ represents N or CH $Z^6$ represents O, S or NH W represents oxygen or sulphur Y represents NH or O B represents a saturated azacyclic ring of the formula

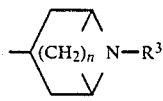 (II)

where n is 2, 3 or 4 and $R^3$ is hydrogen, or (lower)alkyl, or

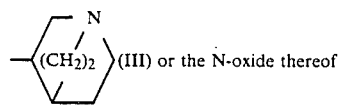 (III) or the N-oxide thereof or

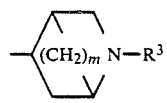 (IV)

where m is 1, 2 or 3 and $R^3$ has the meaning given above or

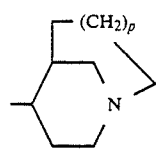 (V)

where p is 0, 1 or 2

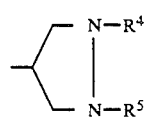 (VI)

where $R^4$ is $R^5$ are each hydrogen or lower alkyl.

* * * * *